US008163721B2

(12) United States Patent
Sachse

(10) Patent No.: US 8,163,721 B2
(45) Date of Patent: Apr. 24, 2012

(54) MANAGEMENT OF BREAKTHROUGH BLEEDING IN EXTENDED HORMONAL CONTRACEPTIVE REGIMENS

(75) Inventor: Andreas Sachse, Berlin (DE)

(73) Assignee: Bayer Pharma AG, Berlin (DE)

( * ) Notice: Subject to any disclaimer, the term of this patent is extended or adjusted under 35 U.S.C. 154(b) by 1526 days.

(21) Appl. No.: 11/118,779

(22) Filed: May 2, 2005

(65) Prior Publication Data

US 2005/0250747 A1 Nov. 10, 2005

Related U.S. Application Data

(60) Provisional application No. 60/566,443, filed on Apr. 30, 2004, provisional application No. 60/575,024, filed on May 28, 2004, provisional application No. 60/577,199, filed on Jun. 7, 2004, provisional application No. 60/638,380, filed on Dec. 27, 2004, provisional application No. 60/660,068, filed on Mar. 10, 2005.

(51) Int. Cl.
*A61K 31/56* (2006.01)

(52) U.S. Cl. ......................................... 514/170; 514/841

(58) Field of Classification Search .................. 514/170, 514/841
See application file for complete search history.

(56) References Cited

U.S. PATENT DOCUMENTS

| | | | |
|---|---|---|---|
| 5,244,096 | A | 9/1993 | Stoner |
| 5,552,394 | A | 9/1996 | Hodgen |
| 5,898,032 | A | 4/1999 | Hodgen |
| RE37,564 | E | 2/2002 | Spona et al. |
| 6,500,814 | B1 | 12/2002 | Hesch |
| 6,620,806 | B2 | 9/2003 | Day et al. |
| 6,632,834 | B2 | 10/2003 | Thompson et al. |
| 6,653,298 | B2 * | 11/2003 | Potter et al. .................. 514/182 |
| 2002/0193356 | A1 * | 12/2002 | Van Beek et al. ............. 514/169 |
| 2003/0018018 | A1 | 1/2003 | Hodgen |
| 2006/0128679 | A1 | 6/2006 | Heithecker et al. |

FOREIGN PATENT DOCUMENTS

| | | |
|---|---|---|
| EP | 1 275 394 A2 | 1/2003 |
| WO | WO-93 13801 | 7/1993 |
| WO | WO-98 08461 | 3/1998 |
| WO | WO-01 15701 | 3/2001 |
| WO | WO 02/22110 * | 3/2002 |

OTHER PUBLICATIONS

The Contraception Report, "Bioequivalence between Brand-Name and Generic OCs," Jun. 2002, 13(2), 6-8.*
Karalis V, Macheras P, Van Peer A, and Shah VP, "Bioavailability and bioequivalence: focus on physiological factors and variability," Pharmaceutical Research, Aug. 2008 (Epub Jun. 2008), 25(8), 1956-1962.*
Thorneycroft IH. Yasmin: the reason why. Eur J Contracept Reprod Health Care. Dec. 2002;7 Suppl 3:13-8; abstract only.*
Fraser et al., MJA, 2003;178(12):621-623.
Apter et al., European Journal of Contraception and Reproductive Health Care, 2003;8:37-51.
Anderson, F. D. et al., "A multicenter, randomized study of an extended cycle oral contraceptive," Contraception, 2003, vol. 68, pp. 89-96.
Clinical Review of NDA 21-544 for Seasonale, Sep. 4, 2003.
Facsimile to Mr. Joseph Carrado Regarding NDA #21-544 Seasonale (Levonorgestrel/ethinyl estradiol) Tablets MACMIS ID#12748, Dec. 29, 2004.
Henzl, M. R. et al., "Avioding Menstruation: A Review of Health and Lifestyle Issues," The Journal of Reproductive Medicine, 2004, vol. 49, pp. 162-167.
Kovacs, G. T. et al., "A trimonthly regimen for oral contraceptives," The British Journal of Family Planning, 1994, vol. 19, pp. 274-275.
Loudon, N. B. et al., "Acceptability of an oral contraceptive that reduces the frequency of menstruation: the tri-cycle pill regimen," British Medical Journal, Aug. 10, 1977, vol. 2, pp. 487-490.
Sulak, P. J. et al., "Acceptance of altering the standard 21-day/7-day oral contraceptive regimen to delay menses and reduce hormone withdrawal symptoms," Am J Obstet Gynecol, 2002, vol. 186, pp. 1142-1149.
Tonkelaar, I. et al., "Preferred Frequency and Characteristics of Menstural Bleeding in Relation to Reproductive Statues, Oral Contraceptive Use, and Hormone Replacement Therapy Use," Contraception, 1999, vol. 59, pp. 357-362.
Coutinho et al., "Comparative study on intermittent versus continuous use of a contraceptive pill administered by vaginal route," Contraception, Jun. 1995, vol. 51, No. 6, pp. 355-358.
Davies et al., "Ovarian activity and bleeding patterns during extended continuous use of a combined contraceptive vaginal ring," Contraception, 1992, vol. 46, No. 3, pp. 269-278.
Davies et al., "The effect of a combined contraceptive vaginal ring releasing ethinyloestradiol and 3-ketodesogestrel on vaginal flora," Contraception, May 1992, vol. 45, No. 5. pp. 511-518.
Mircette Study Group, An open-label, multicenter, noncomparative safety and efficacy study of Mircette, a low-dose estrogen-progestin oral contraceptive, American Journal of Obstetrics and Gynecology, Jul. 1998, vol. 179, Suppl. 1, pp. S2-S8.
Opposition proceedings against EP-0 911 029, Declaration of Anne Szarewski, par. 9-11 dated May 15, 2005.
Rizk et al., Congenital afibrinogenemia: treatment of excessive menstrual bleeding with continuous oral contraceptive, American Journal of Hematology, 1996, vol. 52, No. 3, pp. 237-238 Am. J. Hematology, 1996.
Wiegratz et al., "Long-cycle treatment with oral contraceptives," Drugs, 2004, vol. 64, No. 21, pp. 2447-2462.

* cited by examiner

*Primary Examiner* — Brandon Fetterolf
*Assistant Examiner* — Paul Zarek
(74) *Attorney, Agent, or Firm* — Millen, White, Zelano & Branigan, P.C.

(57) ABSTRACT

The present invention relates to a flexible extended use regimen for a hormonal contraceptive useful to manage bleeding problems associated with fixed extended use of hormonal contraceptives and to a pharmaceutical package containing the respective hormonal contraceptive.

14 Claims, No Drawings

MANAGEMENT OF BREAKTHROUGH BLEEDING IN EXTENDED HORMONAL CONTRACEPTIVE REGIMENS

This application claims the benefit of the filing date of U.S. Provisional Application Ser. No. 60/566,443 filed Apr. 30, 2004, U.S. Provisional Application Ser. No. 60/575,024 filed May 28, 2004, U.S. Provisional Application Ser. No. 60/577,199 filed Jun. 7, 2004, U.S. Provisional Application Ser. No. 60/638,380 filed Dec. 27, 2004, and U.S. Provisional Application Ser. No. 60/660,068 filed Mar. 10, 2005, which are incorporated by reference herein.

The present invention relates to an extended use regimen for a hormonal contraceptive useful to manage bleeding problems associated with currently practiced fixed extended use of hormonal contraceptives, e.g. Seasonale®, and to a pharmaceutical package containing the hormonal contraceptive to be used in such extended regimen.

BACKGROUND

The idea of applying oral contraceptives (OCs) for 21 days followed by a pill break of 7 days to allow withdrawal bleeding was based primarily on the desire to mimic the natural menstrual cycle resulting in 13 menstruations per year. A Dutch telephone survey (Contraception, 1999; 59:357-362) found that the majority of women would prefer either a decreased frequency of bleeding to less than once a month or complete elimination through the extended use of oral contraceptives. Additionally, the majority of women (80.5%) preferred to have either less painful, shorter or less heavy periods or even desired complete amenorrhea.

The first large study on a fixed extended oral contraceptive regimen (90 days=84 days of active pills followed by 6 hormone-free (placebo pills)) was published by Loudon and his colleagues in 1977 (British Medical Journal, 1977; 2:487-490). In this study a monophasic OC [50 µg Ethinyl estradiol (EE)/2.5 mg lynestrenol] was used. Breakthrough bleeding decreased with each three month cycle and no breakthrough bleeding was cited after 9 months of use. Intermenstrual bleeding accounted for 11% of the drop-outs from the study.

Seventeen years later a prospective study on continuous use of 30 µg EE+150 µg LNG (Nordette®) over 84 days followed by one week of placebo was published by Kovacs et al. (The British Journal of Family Planning, 1994; 19:274-275). Of the 203 women who entered the study only 59 (29.1%) completed 12 months of treatment (4×84+7 days). The most frequent reasons for discontinuation were breakthrough bleeding in 73 patients (50.7%) and breast tenderness and headaches in 31 patients (21.5%) each. The drop-out rate was highest during the first extended cycle (13 weeks) in which 34.5% (n=70) of the enrolled women were lost while the drop-out rate in the second to fourth extended cycle (26, 39+52 weeks) amounted to 21.8% (43), 12.3% (25) and 3.0% (6) respectively. The authors state that even though the ability to decrease the incidence of menstruation was appreciated by many women this was negated to some degree by the high incidence of breakthrough bleeding.

Hodgen disclosed a fixed regimen for oral contraceptive use which should maintain the efficacy while providing enhanced control of endometrial bleeding (U.S. Pat. No. 5,898,032). In addition to less menstrual bleeding and patient anemia, higher compliance rates and more lifestyle convenience for patients are listed as advantages of this method. According to the claims, a monophasic combination of an estrogen and progestin is continuously administered for 60-110 consecutive days followed by 3-10 days of no administration (fixed, predetermined duration). The claimed daily amounts of estrogen and progestin are equivalent to 5-35 µg EE and 0.025-10 mg of norethindrone acetate (NETA). Other progestins like levonorgestrel (LNG) or desogestrel are also described.

Hesch (U.S. Pat. No. 6,500,814) discloses a low dose fixed extended cycle product/regimen which according to the inventor surprisingly ensures high contraceptive reliability and prevents inter-menstrual bleeding. Additionally a reduction in OC related side effects (e.g. thrombosis) and a favorable effect on the pre-menstrual syndrome (PMS) are described. Furthermore prophylaxis and treatment of breast cancer are possible with the product according to the invention. Hesch claims continuous and uninterrupted administration of a combined hormonal contraceptive for a period of greater than 110 days. Various natural or synthetic estrogens and progestins are described. When EE is used its dosage is claimed to be between 1-20 µg/day.

Kulmann (WO 02/22110) discloses another process for hormonal contraception which reduces the number of withdrawal bleedings whilst ensuring reliable contraception. The process is characterized by a sequence of successive extended cycles (="taking periods") with increasing duration. Thus for example the patient may start with one taking period of 21 active tablets followed by 7 placebos (21/7) which is followed by a taking period of n×42/7. With the exception of the final taking period the duration of all prior periods is predetermined (fixed). According to the invention it is also possible to successively reduce the hormone dosage (various progestins and/or estrogens listed) between taking periods.

Sulak et al. (Am J Obstet Gynecol, 2002; 186:1142-1149) retrospectively studied the acceptance of extended cycle use in a larger number of patients with hormone withdrawal symptoms. The primary reasons for considering an extended OC regimen were: to decrease symptoms of headache (35%), dysmenorrhea (21%), hypermenorrhea (19%) and premenstrual symptoms (13%). Patients were allowed to alter their standard 21+7 regimen by extending a specific number of weeks such as 6, 9 or 12 or extending until breakthrough bleeding or spotting developed, stopping for 3-7 days and resuming. If they completed 12 weeks of active pills and wished to continue without a hormone-free break they were allowed to do so. There was no limit on the numbers of days a patient could extend. All patients were prior pill users taking monophasic pills with 30-35 µg ethinyl estradiol and one of the following progestins: norethindrone, levonorgestrel, norgestimate or desogestrel. Of the 267 patients who initiated the extended cycle regimen 57 (21%) chose to stop using OCs for various reasons like worsening in side effects including nausea, headache, acne, leg cramps, high blood pressure, yeast infections, breakthrough bleeding and PMS (24 patients) and a desire for pregnancy (13 patients). Of the 210 patients who continued to use OCs, 38 (18%) chose to return to the standard 21/7 regimen most commonly due to breakthrough bleeding (11 patients), breakthrough spotting (9) and heavy withdrawal bleeding (2 patients). The typical pattern of extended OC use by patients was 12±12 weeks (mean±SD) weeks of active pills with a median of 9 weeks and a range up to 104 weeks. The typical pill free interval was reported as 6±2 days with a median of 5 days and a range of 0-7 days.

Recently the results of a phase III multicenter 1-year trial on a fixed extended OC regimen with a 91-day cycle days versus a normal 28-day cycle (21 days active+7 placebo pills) have been published by Anderson et al. (Contraception, 2003; 68:89-96). The extended cycle regimen according to Hodgen (U.S. Pat. No. 5,898,032) was found to be effective in preventing pregnancy and had a safety profile comparable to the 28 day regimen (30 µg EE/150 µg LNG each). However, the extended cycle regimen patients reported a greater number of unscheduled (breakthrough) bleeding amounting to 37.6 days compared to 18.3 days for the 28-day regimen. The total days of bleeding unscheduled+scheduled (=menstrual bleeding) during the study year (364 days) were 48.2 days for the extended cycle compared to 50.8 days for the standard cycle. It was reported that for the extended cycle breakthrough bleeding (BTB) decreased with each successive cycle (84+7 each) from a median of 12 days during cycle 1 to a median of 4 days during cycle 4.

The most common reasons given for study discontinuation were bleeding, increased weight, mood swings and acne (=adverse events). Discontinuation due to unacceptable bleeding accounted for 7.7% of the 91-day regimen patients compared to 1.8% in the 28-day regimen group. The total drop out rates amounted to 40.6% and 28.8% respectively.

The product which was tested in this study has been launched in the US in September 2003 (Seasonale®, Barr Laboratories). In the product label it is stated that the patients on the 91-day treatment cycle should initially expect to have more bleeding or spotting between their menstrual periods than if they were taking a 28-day treatment cycle. Finally it is pointed out that intake of Seasonale® should not be stopped because of the bleeding.

In the Clinical Review of NDA 21-544 (Sep. 4, 2003) for Seasonale® additional results on Seasonale® Ultra-Lo (20 µg EE/100 µg LNG daily) are reported. It was observed that the fixed (84+7 days) extended regimen with a lower EE dose results in an even worse bleeding control. Thus the drop out rates for Seasonale® Ultra-Lo due to bleeding problems increased to 13.8% compared to 7.7% for Seasonale® (table 23). In comparison the drop out rate for the corresponding standard cycle (21+7 days) product Levlite® is reported to amount to only 0.9% in the same study.

Among the most frequently reported adverse events related to bleeding, menorrhagia was most often found. The respective values amount to: 11.6% for Seasonale®, 14.9% for Seasonale® Ultra-Lo and 2.6% for Levlite® (table 24). It has to be noted that the MedDRA term menorrhagia which was used for this study incorporates a number of adverse events related to vaginal bleeding such as intermittent, unexpected, breakthrough etc.

Similar observations can be drawn from the comparison between Loestrin 30 (30 µg EE/1.5 mg NETA) and Loestrin 20 (20 µg EE/1.0 mg NETA). Loestrin 30 is a widely used oral contraceptive which gives excellent cycle control. It is well known that Loestrin 30 is suitable for administration in an extended use regimen. Loestrin 20 gives very poor cycle control (Szarewski 1991, Szarewski & Guillebaud 1994, 1998, 2000, 2002, Wilkinson & Szarewski 2003) and therefore cannot be recommended for fixed extended use (Opposition proceedings against EP 0 911 029 B1, Declaration of Anne Szarewski, par. 9-11).

Spona et al. (U.S. Pat. No. RE37,564 E) teach a combination product for oral contraception comprising 23 or 24 dosage units each containing an estrogen (20 µg EE) and a progestin (2.5 to 3.0 mg drospirenone or 1 to 2 mg cyproterone acetate) and 5 or 4 blanks or placebos to complete the 28 days cycle. Such products result in a pronounced ovarian suppression without frequent follicular maturations.

Hodgen (U.S. Pat. No. 5,552,394) describes a method of female contraception which addresses the problem of increased bleeding problems for lower dose (estrogen+progestin) standard cycle (28-days regimen) OCs during the early months of use. Thus the overall instances of bleeding control problems for OCs have increased as the doses were reduced as reflected by the increase in breakthrough bleeding (untimely flow or spotting). By administering a monophasic combination of an estrogen and progestin for 23-25 consecutive days followed by a 2-5 day pill free period a reduced incidence of breakthrough bleeding could surprisingly be observed after the first 28-day cycle. The claimed daily amounts of estrogen and progestin are equivalent to about 1-35 µg EE and about 0.025-10 mg NETA, respectively, in which the weight ratio of estrogen to progestin is at least 1:45 calculated as EE to NETA. When other estrogens or progestins are used an adjustment in the used amounts based on the relative potencies should be made. Thus 3.5 mg of NETA are roughly equivalent to 1 mg of LNG or desogestrel or 0.7 mg of gestodene.

According to the prior art in the field of extended cycle regimens (see above) it was assumed that even for low dose (estrogen) hormonal contraceptives, stable extended cycles (i.e. absence of inter-menstrual bleeding) of fixed duration could be obtained and maintained even during the first year of administration. However, the published clinical data do not support these claims. Just to the contrary it was observed in large controlled clinical studies that administration of a low dosed estrogen composition (<30 µg EE) in a fixed extended cycle regimen leads to far higher bleeding complications and thus drop out rates in clinical practice compared to extended cycle regimens with higher EE dose ($\geq$30 µg). Most notably the bleeding complications for fixed extended cycle regimens in general were found to be much higher than for the corresponding standard cycle (21+7 days) regimens.

In a recent review on the available compositions and methods for extended OC use by Henzl and Polan it was concluded that either alternative routes of application to the oral route or use of different hormonal agents than those used in the available products should be pursued to improve some of the deficiencies of the current schedule, breakthrough bleeding and spotting in particular (Journal of Reproductive Medicine 2004; 49:162-174).

Thus there is a clear need for an extended OC regimen which reduces or eliminates the bothersome intermenstrual bleeding (breakthrough bleeding and/or spotting) problems observed for fixed extended regimens. Such regimen would allow to comply with the desire of the majority of women who would prefer either a decreased frequency of menstrual bleeding to less than once a month or complete elimination through the extended use of oral contraceptives. There is still further need that such extended regimen should preferably be a low dosed (especially estrogen) regimen.

The low dose aspect is of special importance in such continuous administration regimens in order to minimize the total (annual) hormone exposure to compensate for the additional hormone administration due to the reduced number of hormone free phases compared to the standard cycle (21+7 days) regimen.

By allowing shorter pill breaks such an extended regimen should further minimize the intermenstrual and/or menstrual bleeding and additionally diminish disorders which occur during the hormone free intervall, as for instance symptoms related to PMS (premenstrual syndrome) incl. headaches, dysmenorrhea and pelvic pain, hypermenorrhea and acne (i.e. menstruation related disorders).

Furthermore such an extended OC regimen should offer flexibility regarding its duration to allow the patients to adapt the regimen (i.e. time and frequency of menstruation) to their specific biological/medical and individual needs.

Additionally such a flexible extended OC regimen should potentially allow a further reduction of estrogen and/or progestin dose compared to the available standard cycle products (e.g. 21+7 or 24+4 days).

Finally such a contraceptive regimen should offer additional therapeutic benefits (e.g. a positive influence on endometriosis, PMS, PMDD, polycystic ovarian syndrome (PCOS)) not directly related to bleeding disorders to the patients. Consequently such regimen should also be suitable for treatment of endometriosis, PMS, PMDD or polycystic ovarian syndrome (PCOS)

DETAILED DESCRIPTION OF THE INVENTION

It could be shown that the problem of intermenstrual bleeding during fixed use of extended hormonal contraceptives in a female surprisingly can be avoided by a new contraceptive method (estrogen/progestin combination or regimen) which comprises administration of a monophasic contraceptive containing an estrogen and a progestin to the woman over at least a first minimum period until the female will observe unacceptable bleeding upon which the woman initiates a voluntary pill break of a maximum duration of 6 days (=managed bleeding).

The invention relates to a method for female hormonal contraception which comprises the continuous administration of a monophasic preparation of ethinyl estradiol in an amount of 5 to <30 μg or another estrogen in an amount equivalent to 5 to <30 μg ethinyl estradiol and a progestin in a contraceptive amount to the female for a first minimum period for as long as desired by the woman or until unacceptable bleeding is observed upon which the female initiates an active preparation break, e.g. hereinafter, "pill" break of 1 to 6 days and wherein the pill break is followed by at least one further administration cycle of at least the duration of the first minimum period. (The following description in terms of pills is for convenience only. The invention includes other administration modes (i.e. routes of application+types of drug preparations) as mentioned herein).

The managed bleeding approach means that a pill break (=hormone free phase or active preparation break) is initiated upon unacceptable bleeding which is characterized by being bothersome to the women on the extended cycle regimen. Unacceptable bleeding is most often observed as spotting (not requiring sanitary protection) which does not resolve spontaneously. Alternatively/additionally breakthrough bleeding (requiring sanitary protection) may occur. In case of such bothersome bleeding the women may initiate a pill break after 1 to 10 consecutive days of intermenstrual bleeding, preferably after 2 to 8 and most preferably after 3 to 5 days.

The shortened pill break of 1 to 6 days leads to a further reduction in intermenstrual and/or menstrual bleeding and menses related disorders, as for instance headaches, PMS, PMDD, dysmenorrhea, hypermenorrhea and endometriosis.

Preferred pill breaks [i.e. no pill intake or placebo (inactive) pills] are 3 or 4 days.

In a preferred embodiment the pill break due to unacceptable bleeding is only initiated after breakthrough bleeding. In even more preferred cases the pill break is fixed to a single number of days.

The minimum active intake period is between 7 and 59 days.

Preferred are minimum intake periods of 14 to 35 days, more preferred of 21 to 28 days and most preferred of 21 to 24 days.

After a pill break (hormone free phase) was taken the patient has to start over again using the active pills for at least the minimum intake period, preferably for at least 14-35 days, more preferably for 21 to 28 days and most preferably for 21 to 24 days, before taking the next break.

In preferred cases these subsequent cycles can be extended for longer periods (duration not predetermined) than the preceding cycle due to stabilization of the endometrium. However, in case of unacceptable bleeding during the minimum intake period or due to other considerations the woman may choose not to extend the subsequent cycle but rather stay with the minimum intake interval (e.g. 14-35 days) for several consecutive cycles.

If no bleeding problems occur, the cycle can be extended for as long as desired by the woman which represents the maximum cycle length. In preferred cases a pill break will only be taken once induction of menstruation is desired by the woman e.g. to assure absence of pregnancy. Typically the woman will have to consult her physician/health care professional regarding the suitable cycle length who will instruct her accordingly based on the individual patient situation/needs and within the respective range of the product label.

The maximum extended cycle length can usually be reached within 2 years of start of the managed bleeding regimen. In preferred cases, the maximum cycle length is already reached after 6 to 12 months. Due to legal/regulatory requirements the maximum cycle length may be limited to a fixed maximum (e.g. 77-91, 112-126 days, 175-189 days or 336-364 days) depending on the available long-term safety data (preclinical and/or clinical).

Such regimens according to the invention will result in markedly lower drop out rates in clinical settings due to bleeding problems compared to, e.g. Seasonale®. Consequently, such regimens will also lead to high compliance and a high acceptance by the patients applying this method of contraception.

The preferred estrogen is ethinyl estradiol (EE) in a daily amount of 5 to <30 μg, more preferably 10 to 25 μg and most preferably 20 μg.

Estradiol and its esters can also be used as the estrogen. The daily amount of estradiol to be administered is 0.5 to 3 mg, preferably 1 to 2 mg.

Additionally synthetic estrogens can be used at doses equivalent to 5 to <30 μg EE (i.e. equivalent with regard to inhibition of gonadotropins and ovulation as well as proliferative effects on the endometrium and vaginal epithelium).

As progestins according to the invention all progestins known to be suitable for their use in hormonal contraception can be used.

Preferably, drospirenone, dienogest, levonorgestrel, gestodene, desogestrel, 3-ketodesogestrel, norethindrone acetate, norgestimate, norelgestromin, trimegeston, cyproterone acetate or etonogestrel are used.

Of these, drospirenone which has a pronounced effect on premenstrual symptoms, PMDD, dysmenorrhea and on acne and dienogest which exerts an excellent cycle control and also has a pronounced effect on acne, dysmenorrhea and endometriosis are even more preferred for use in extended regimens according to the invention.

The progestin doses to be administered daily are the amounts which are known to be effective for contraception. For the progestins specifically mentioned these daily amounts are: drospirenone 1.0 to 4.0 mg, preferably 2.5 to 3.5 mg, dienogest 0.5 to 3.0 mg, preferably 1.0 to 2.5 mg, levonorgestrel 0.050 to 0.15 mg, gestodene 0.04 to 0.1 mg, desogestrel 0.075 to 0.15 mg, 3-ketodesogestrel (etonogestrel) 0.075 to 0.15 mg, norethindrone acetate 0.5 to 1 mg, norgestimate 0.1 to 0.25 mg, norelgestromin 0.075 to 0.15 mg, trimegeston 0.1 to 0.5 mg or cyproterone acetate 1 to 2 mg.

In a method according to the invention the product to be administered will be formulated and administered conventionally, i.e. all standard routes of application, including the various known types of drug preparations (delivery systems), e.g. transdermal patches, IUSs and vaginal rings, and other formulations to be applicable to hormonal contraception can be used to perform the invention.

The route of oral administration is preferred.

The product to be used in the method according to the invention is provided in a packaging form which supports the managed bleeding approach and ensures compliance. In preferred cases electronic means are used in such a packaging solution to remind the woman of pill intake. The package of such product includes a special patient information instructing the patient how to use the product according to the claimed method.

Advantages of the managed bleeding method compared to fixed extended cycle regimens and/or standard cycle (e.g. 21+7 or 24+4) products according to the invention include:

- achievement of overall improved bleeding rate (=reduction of total number of bleeding days), potentially even during the first year of administration, and/or
- reduction in intermenstrual bleeding (breakthrough bleeding and/or spotting), and/or
- improved compliance/reduced rate of discontinuation, and/or
- improved flexibility of regimen in relation to needs of user, and/or
- reduction in cycle and/or menstruation associated disorders such as PMS, PMDD, headaches (migraine), dysmenorrhea and pelvic pain, hypermenorrhea, endometriosis, PCOS and acne, and/or
- reduction in side effects (e.g. nausea, headache, acne, high blood pressure, mood swings, weight gain, bleeding) and/or
- improved quality of life.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The following examples shall explain the invention in further detail without limiting the invention to these special examples:

Example 1

The following clinical protocol can be performed to examine the bleeding profile obtained for the managed bleeding approach of the present invention. This protocol is proposed to demonstrate the superior bleeding properties of an extended cycle OC regimen with a low EE dose compared to a fixed extended cycle regimen. For practicality reasons (i.e. study duration) the maximum cycle length in the protocol is standardized to a fixed value between 112-140 days which will be fixed prior to start of the study (e.g. 120 days).

A one-year, multicenter, open, randomized, parallel-group comparison study in young fertile women of 18-35 years is performed with an OC containing 20 µg ethinyl estradiol as beta-cyclodextrin clathrate and 3 mg drospirenone. Standard inclusion and exclusion criteria for OC studies are used.

In the present protocol a fixed extended cycle regimen is compared with a flexible (managed bleeding) regimen which allows a 4 day pill break in case of 3 consecutive days of breakthrough bleeding or spotting after a minimum intake of active pills for 24 days. After each pill break a new extended cycle with a minimum duration of 24 days and a maximum duration of e.g. 120 days is started. Additionally a standard cycle OC (24+4) is included as comparator.

Bleeding pattern and cycle control parameters are evaluated via an electronic or a paper diary. The number of unintended pregnancies is evaluated (Pearl Index, Life table analysis).

Additionally standard safety parameters for OCs are studied.

The number of subjects is determined based on biometric considerations with at least 150 patients in each study arm.

Example 2

Potential Label for the Product Tested According to Example 2

"Product" must be taken daily for a minimum of 24 days, and may be taken daily up to a maximum of 120 days, before a 4-day pill-free break is taken. In case of unacceptable bleeding(/At any time) between day 25 and the scheduled end of tablet intake (day 120), a 4-day pill-free break may be taken. After a 4-day pill-free break, a new cycle is started and "Product" must again be taken for a minimum of 24 days and up to a maximum of 120 days before the next 4-day pill-free break is taken.

Example 3

The following clinical protocol is used to demonstrate the superior bleeding properties of an extended cycle OC regimen with a low EE and LNG dose compared to the corresponding normal cycle OC. For practicality reasons (i.e. study duration) the maximum cycle length in the protocol is standardized to a fixed value between 77 and 126 days which will be fixed prior to start of the study (e.g. 84 days).

A one-year, multicenter, open, randomized, parallel-group comparison study in young fertile women of 18-40 years is performed with an OC containing 20 µg ethinyl estradiol and 100 µg levonorgestrel. Standard inclusion and exclusion criteria for OC studies are used. In the present protocol a flexible (managed bleeding) regimen according to the invention is compared to a corresponding standard cycle regimen (21+7, e.g. Alesse®). The managed bleeding regimen allows a 3-4 day pill break in case of 1 to 10 consecutive days of breakthrough bleeding or spotting after a minimum intake of active pills for 21 days. After each pill break a new extended cycle with a minimum duration of 21 days and a maximum duration of e.g. 84 days is started.

Bleeding pattern and cycle control parameters are evaluated via an electronic or a paper diary. The number of unintended pregnancies is evaluated (Pearl Index, Life table analysis).

Additionally standard safety parameters for OCs are studied.

The number of subjects is determined based on biometric considerations with at least 150 patients in each study arm.

COMPARATIVE EXAMPLE

OC users are counselled by their Ob/Gyn physician on extending the active pill interval of standard OCs with a minimum intake of 21 days and a shortened pill-break (no active pills) of 3-4 days to manage bleeding (i.e. when bothersome breakthrough bleeding or spotting occurs) if desired. Monophasic pills with 35 μg EE or less and various progestins (norethindrone, levonorgestrel, desogestrel, norgestimate+ drospirenone) are used.

Approximately 95% of the counseled patients choose to alter their standard 21+7 day cycle regimen for various reasons including: premenstrual symptoms (45%), dysmenorrhea/pelvic pain (40%), heavy withdrawal bleeding (36%), menstrual associated headaches (35%), convenience (13%) acne associated with menses (10%) and others (15%).

Approximately 70% of the patients who initiate an extended OC regimen continue beyond two years. Of those approximately 50% adopt an extended pattern of 13 weeks or greater of active pills with 88% using a pill-break below 4 days.

In contrast to this 25% eventually quit using OCs for one or more reasons including: side effects (23%), desire to become pregnant (23%) medical conditions (12%), hysterectomy (12%) and others (30%). The most common side effect in this group is breakthrough bleeding or spotting (=60%, or 3.5% of the total number of patients originally extending).

Just six per-cent of the patients who start an extended OC regimen return to the standard 21+7 regimen mainly due to side effects (60%). The most common side effect is breakthrough bleeding or spotting (35%, or 1.2% of the total number of patients on an extended cycle).

In total only 4.7% of the patients who attempt an extended cycle regimen using the managed bleeding approach discontinue for bothersome bleeding.

The entire disclosures of all applications, patents and publications, cited herein and of corresponding U.S. Provisional Application Ser. No. 60/566,443 filed Apr. 30, 2004, U.S. Provisional Application Ser. No. 60/575,024 filed May 28, 2004, U.S. Provisional Application Ser. No. 60/577,199 filed Jun. 7, 2004, U.S. Provisional Application Ser. No. 60/638,380 filed Dec. 27, 2004, and U.S. Provisional Application Ser. No. 60/660,068 filed Mar. 10, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for oral contraception in a woman comprising the following monophasic, extended, cyclic regimen:
   (1) administering to said woman an oral contraceptive, which comprises 20 μg of ethinyl estradiol and 3 mg of drospirenone, daily for a first period of 24 days, and thereafter administering said oral contraceptive daily for a second period of a maximum of 96 days during which (a) said woman initiates a break of 3-6 days in which the oral contraceptive is not administered, or (b) if no such break is initiated within said maximum of 96 days, said woman initiates a break period of 3-6 days at the end of the 96 day period, and
   (2) after said break period, administering said oral contraceptive with an administration/break pattern in accordance with (1) above,
   wherein a second period is at least one day long.

2. A method according to claim 1 wherein said break is 4 days long.

3. A method according to claim 2 wherein in an administration/break pattern (1) a second period of up to 96 days long in which said oral contraceptive is administered is longer than said first 24 day period.

4. A method according to claim 2 wherein the woman stops administering said oral contraceptive in a second period of up to 96 days long upon the occurrence of breakthrough bleeding.

5. A method according to claim 2 wherein the woman does not stop administering said oral contraceptive in a second period of up to 96 days long.

6. A method of claim 2 wherein in an administration/break pattern (1) a second period of up to 96 days long in which said oral contraceptive is administered is at least as long as the first 24 day period.

7. A method according to claim 2 wherein the woman stops administering said oral contraceptive within said period of up to 96 days long.

8. A method according to claim 2 wherein the woman stops administering said oral contraceptive within said period of up to 96 days long in the absence of bleeding problems.

9. A method for management of unacceptable bleeding during oral contraception in a woman comprising the following monophasic, extended, cyclic regimen:
   (1) administering to said woman an oral contraceptive, which comprises 20 μg of ethinyl estradiol and 3 mg of drospirenone, daily for a first period of 24 days, and thereafter administering said oral contraceptive daily for a second period of a maximum of 96 days during which (a) said woman, upon occurrence of bleeding initiates a break of 3-6 days in which the oral contraceptive is not administered, or (b) if no such break is initiated within said maximum of 96 days, said woman initiates a break period of 3-6 days at the end of the 96 day period, and
   (2) after said break period, administering said oral contraceptive with an administration/break pattern in accordance with (1) above,
   wherein a second period is at least one day long.

10. A method according to claim 9 wherein said break is 4 days long.

11. A method according to claim 10 wherein in an administration/break pattern (1) a second period of up to 96 days long in which said oral contraceptive is administered is longer than said first 24 day period.

12. A method according to claim 10 wherein said bleeding is breakthrough bleeding.

13. A method according to claim 10 wherein the woman does not stop administering said oral contraceptive in a second period of up to 96 days long.

14. A method according to claim 10 wherein in an administration/break pattern (1) a second period of up to 96 days long in which said oral contraceptive is administered is at least as long as the first 24 day period.

* * * * *